United States Patent
Rieter et al.

(10) Patent No.: US 9,623,227 B2
(45) Date of Patent: Apr. 18, 2017

(54) TUBING SET HAVING AN INSERT FOR THE INFUSION OF DRUGS

(75) Inventors: Reinhold Rieter, Crema (IT); Massimo Fini, Mirandola (IT)

(73) Assignee: PRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 449 days.

(21) Appl. No.: 13/498,681

(22) PCT Filed: Sep. 30, 2010

(86) PCT No.: PCT/EP2010/064559
§ 371 (c)(1),
(2), (4) Date: Mar. 28, 2012

(87) PCT Pub. No.: WO2011/039306
PCT Pub. Date: Apr. 7, 2011

(65) Prior Publication Data
US 2012/0184939 A1    Jul. 19, 2012

(30) Foreign Application Priority Data
Sep. 30, 2009    (EP) ..................... 09171888

(51) Int. Cl.
*A61M 37/00*    (2006.01)
*A61M 39/02*    (2006.01)
(Continued)

(52) U.S. Cl.
CPC ................ *A61M 39/02* (2013.01); *A61J 1/06* (2013.01); *A61M 1/342* (2013.01);
(Continued)

(58) Field of Classification Search
CPC ........ A61M 39/08; A61M 39/10; A61M 1/36; A61M 5/1409; A61M 5/162; A61M 1/342;
(Continued)

(56) References Cited

U.S. PATENT DOCUMENTS 5,015,226 A    5/1991    Polaschegg
5,135,489 A *  8/1992    Jepson et al. .................. 604/48
(Continued)

FOREIGN PATENT DOCUMENTS

CN    2059839    8/1990
CN    2654131    11/2004
(Continued)

*Primary Examiner* — Philip R Wiest
*Assistant Examiner* — Ariana Zimbouski
(74) *Attorney, Agent, or Firm* — Jacobson Holman, PLLC.

(57) ABSTRACT

A tubing set suitable for use in co-operation with a machine for carrying out a hemodialysis treatment of a patient's blood includes a blood out-tube for supplying the blood from the patient to a filter, a blood in-tube for supplying the blood from the filter back to the patient, and a substitution tube connected to the blood in-tube or the blood out-tube suitable for providing a substitution fluid in the patient's blood. The substitution tube includes an insert for the infusion of drugs, with the insert being configured to cooperate with a vial. A method of delivering drugs includes use of the tubing set, including the substitution tube, the insert, and the vial.

7 Claims, 11 Drawing Sheets

(51) Int. Cl.
*A61J 1/06* (2006.01)
*A61M 1/34* (2006.01)
*A61M 5/14* (2006.01)
*A61M 5/142* (2006.01)
*A61M 5/162* (2006.01)
*A61M 39/24* (2006.01)

(52) U.S. Cl.
CPC ........ *A61M 1/3431* (2014.02); *A61M 1/3437* (2014.02); *A61M 5/1409* (2013.01); *A61M 5/142* (2013.01); *A61M 5/162* (2013.01); *A61M 2039/0205* (2013.01); *A61M 2039/242* (2013.01)

(58) Field of Classification Search
CPC ...... A61M 1/34; A61M 1/3431; A61M 39/14; A61M 2039/0205; A61M 39/04
USPC .......................................... 604/6.06–6.15, 21
See application file for complete search history.

(56) References Cited

U.S. PATENT DOCUMENTS

| | | | |
|---|---|---|---|
| 5,676,346 A * | 10/1997 | Leinsing | 251/149.1 |
| 5,693,008 A | 12/1997 | Brugger et al. | |
| 5,722,399 A * | 3/1998 | Chevallet et al. | 600/485 |
| 5,928,177 A * | 7/1999 | Brugger et al. | 604/6.11 |
| 5,983,947 A | 11/1999 | Utterberg | |
| 6,387,069 B1 * | 5/2002 | Utterberg | 604/4.01 |
| 2002/0188273 A1 * | 12/2002 | Ko | 604/403 |
| 2003/0187420 A1 * | 10/2003 | Akerlund | A61M 5/1409 604/408 |
| 2005/0215976 A1 * | 9/2005 | Wallen | 604/500 |
| 2007/0149926 A1 * | 6/2007 | Moberg et al. | 604/152 |
| 2007/0175828 A1 * | 8/2007 | Goedje et al. | 210/646 |
| 2009/0101552 A1 | 4/2009 | Fulkerson et al. | |
| 2009/0107335 A1 | 4/2009 | Wilt et al. | |
| 2009/0107902 A1 * | 4/2009 | Childers | A61M 1/16 210/196 |
| 2009/0326481 A1 * | 12/2009 | Swisher et al. | 604/246 |
| 2010/0152669 A1 * | 6/2010 | Rosenquist | A61M 39/10 604/192 |
| 2010/0168643 A1 * | 7/2010 | Frugier et al. | 604/6.16 |

FOREIGN PATENT DOCUMENTS

| | | |
|---|---|---|
| CN | 2010060056 | 1/2008 |
| CN | 201171832 | 12/2008 |
| EP | 1 909 866 | 4/2008 |
| WO | WO 90/12606 | 11/1990 |
| WO | WO 99/61093 | 12/1999 |
| WO | WO 2007/012915 | 2/2007 |
| WO | WO 2008/106191 | 9/2008 |
| WO | WO2008135193 | * 11/2008 |

* cited by examiner

TUBING SET HAVING AN INSERT FOR THE INFUSION OF DRUGS

CROSS-REFERENCE TO RELATED APPLICATIONS

This is a national stage of PCT/EP10/064559 filed Sep. 30, 2010 and published in English, which claims the priority of European number 09171888.2 filed Sep. 30, 2009, hereby incorporated by reference.

BACKGROUND OF THE INVENTION

1. Field of Invention

The invention concerns a tubing set comprising an insert for the infusion of drugs in extracorporeal circuits, in particular a tubing set intended to be used with hemodialysis machines. The invention further concerns a vial suitable for being fitted onto the insert.

2. Description of the Prior Art

In therapeutic treatment that require an extracorporeal circulation it is often necessary to administer different drugs or therapeutic substances to the patient. The presence of the tubing set advantageously makes it possible to avoid the administering of the drug taking place through puncture carried out directly on the patient himself.

As an example, hereafter we consider hemodialysis treatment, without for this reason limiting the scope of the invention to this specific application.

Most of the recent hemodialysis machines, are arranged also for carrying out another treatment, called hemofiltration. Hemofiltration is a renal replacement therapy which is used almost exclusively for acute renal failure. During hemofiltration, a patient's blood is passed through a filter where waste products and water are removed. Due to the water removal, a substitution fluid is needed in addition to the blood which is returned to the patient. Hemofiltration is sometimes used in combination with hemodialysis, originating the so called hemodiafiltration treatment.

In view of the above, recent hemodialysis machines, are provided with a specific circuit intended to deliver the substitution fluid.

In the following, for ease of description, reference will be made to hemodialysis only, however hemofiltration and hemodiafiltration should also be considered within the scope of the present invention.

During such treatments it often becomes necessary to administer different drugs or therapeutic substances, like for example iron, heparin, erythropoietin and vitamin D. The infusion of such substances in the extracorporeal circuit is currently carried out through conventional syringes. The substance is drawn from the vial in which it is supplied by the producer and is then injected into a special puncturable cap provided along the tubing set. Thus there is a double transfer of the substance: firstly from the vial to the syringe and then from the syringe to the circuit.

Such an operation therefore requires the use of disposable materials, such as the syringe and the respective needle, just to transfer the substance from the vial to the tubing set. Moreover, the use of needles always carries the risk of the service staff being pricked.

Furthermore, during the infusion of some therapeutic substances in the patient's blood, attention must be paid in order to avoid hemolysis.

Finally, some of the quoted substances need to be administered slowly, over a few minutes. From this it can easily be understood how the administering of various substances to more than one patient represents a considerable workload for the nursing staff responsible for the treatment.

Two automated processes for delivery of heparin are disclosed in the prior art. A specific pump for acting on the heparin syringe is disclosed in EP 1 909 866. According to this first solution, this specific pump can be used only for heparin, while it can not be used for any other medicament.

A different solution is disclosed in U.S. Pat. No. 5,015,226 wherein the negative pressure induced in the blood conduit by the blood pump is used for sucking the heparin out of the vial. Since the blood pump is located upstream the dialysis filter, this method is only usable with medicaments which can not pass the filter membrane. Furthermore, in such process can be used collapsible vials only, since there is no possibility to effectively suck a medicament out of a rigid vial by way of the negative pressure.

Other tubing sets and the related assemblies for the infusion of substances in the extracorporeal circuit are described in detail in documents U.S. Pat. No. 5,693,008; U.S. Pat. No. 5,983,947; US 2009/0101552 and WO 2008/106191.

SUMMARY OF THE INVENTION

The purpose of the present invention is therefore to at least partially solve the drawbacks highlighted in relation to known tubing sets for infusion.

A task of the present invention is to avoid the double transfer of the substance.

Another task of the present invention is to make it possible to avoid the use of conventional syringes and the respective needles.

A task of the present invention is to allow the infusion of therapeutic substances without any risk of hemolysis for the patient's blood.

Another task of the present invention is to allow automated processes for the delivery of any medicament, e.g. to allow slow administering of the substances that require it without needing the active presence of the service staff to do so.

A task of the present invention is to allow even simultaneous infusion of a plurality of drugs.

The purpose and the tasks indicated above are accomplished by a tubing set, an insert, a vial, and a method as described herein.

BRIEF DESCRIPTION OF THE DRAWINGS

The characteristics and the further advantages of the invention shall become clear from the following description of some embodiments, given for indicating and not limiting purposes with reference to the attached drawings, in which.

DETAILED DESCRIPTION OF THE PREFERRED EMBODIMENTS

Further scope of applicability of the present invention will, become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

With specific reference to the enclosed figures, the reference 100 indicates a hemodialysis machine where a patient's blood is passed through a filter to remove waste products and water. The machine 100, known per se, is provided with a disposable tubing set 126 which comprises:
- a blood out-tube 102 for supplying the blood from the patient to a filter 106 of the machine 100;
- a blood in-tube 114 for supplying the blood from the filter 106 back to the patient; and
- a substitution tube 116 connected to one of said blood in-tube 114 or blood out-tube 102 suitable for providing a substitution fluid in the patient's blood.

In the tubing set 126 according to the invention, the substitution tube 116 comprises an insert 30 for the infusion of drugs.

According to some embodiment of the invention, the tubing set 126 further comprises a drain tube 108 for discharging the waste fluid originating from the filter 106; and a dialysate tube 112 for supplying a dialysate to the filter 106.

According to some embodiment of the invention, the blood out-tube 102 is suitable to co-operate with a blood pump 104 of said machine 100. Similarly, the drain tube 108 and the substitution tube 116 can be suitable to co-operate with a drain pump 110, and a substitution pump 118, respectively, of the machine 100.

According to an embodiment of the invention, an assembly 28 for the infusion of drugs comprises the insert 30, placed along the substitution tube 116, and a vial 34. The insert 30 preferably comprises:
- a main duct 31 suitable for ensuring the fluid continuity of the substitution tube 116;
- at least one access point 32 comprising mechanical connection means 36 and hydraulic connection means 38, suitable for being connected to the vial 34 containing a therapeutic substance;
- a membrane 40 suitable for ensuring the sterility of the hydraulic connection means 38 and intended to be broken or removed in order to be able to couple the vial 34.

The vial 34, suitable for containing a therapeutic substance, preferably comprises:
- mechanical connection means 42 and hydraulic connection means 44, suitable for being fitted onto the access point 32 of the insert 30;
- a membrane 46 suitable for ensuring the sterility of the hydraulic connection means 44 and intended to be broken or removed in order to be able to fit the vial 34 onto the respective access point 32.

The access points 32 are intended to receive the fitting of the vial 34, without the need of the intermediate transfer by means of a conventional syringe and the respective needle.

The single vial 34 can be fitted onto the respective access point 32 through any coupling that allows an airtight fit even in the presence of pressure difference between the inside and the outside of the circuit 26. Such a result can be obtained through a threaded coupling, a bayonet coupling, a snap coupling, an interference coupling or similar. It should be noted how the access points 32 according to the invention do not use the solution of the puncturable cap. Indeed, it has been considered that the use of the syringe and relative needle is disadvantageous overall due to the costs connected to the consumed material, the time required by the relative operations and the risks of the service staff being pricked through their use.

What has been stated above does not of course rule out the possibility of an insert 30 according to the invention comprising, alongside the access points 32 intended for the vial 34, also one or more known puncturable caps. Such a provision ensures that the insert 30 according to the invention is also compatible with the prior art and thus allows possible stocks not specifically intended for use in combination with the insert 30 to be used up.

Figure 11:
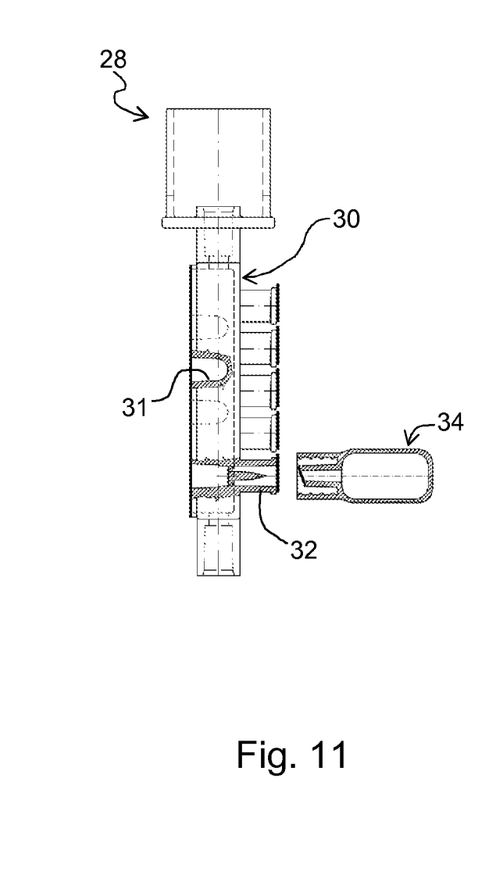
FIG. 11 represents a side view partially in section of the insert of FIG. 9 and of a vial suitable for being fitted onto it.
Figure 12:
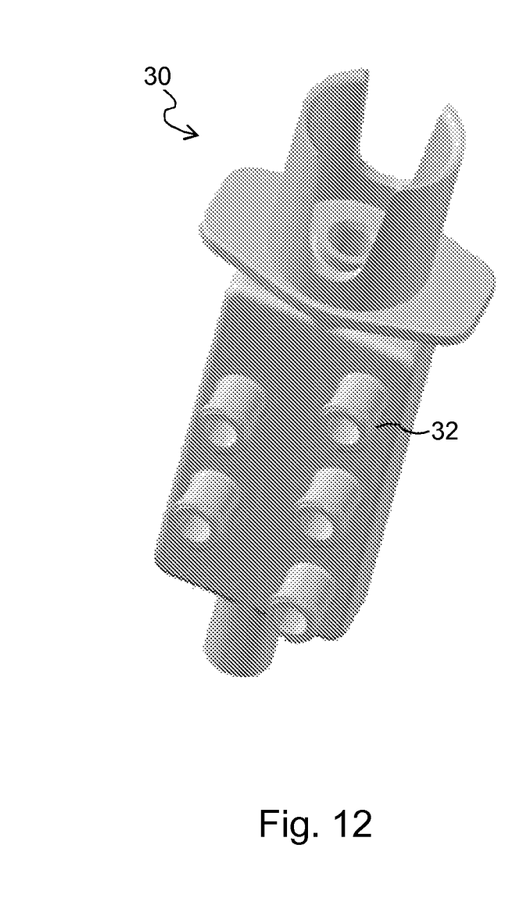
FIG. 12 represents a perspective view of the insert of FIG. 9.
Figure 13:
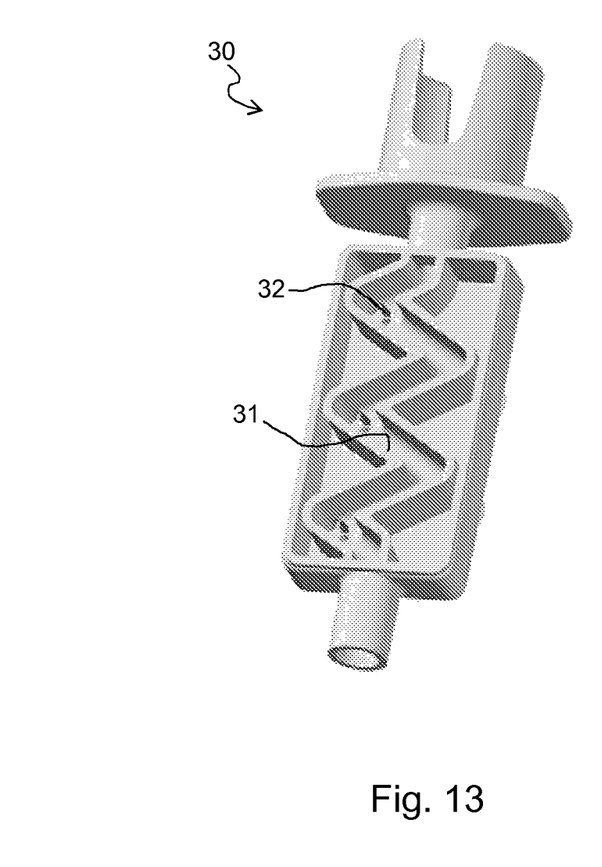
FIG. 13 represents a view similar to that of FIG. 12 in which part of the outer cover of the insert has been removed.

In accordance with some embodiments, each of the access points 32 is designed for a single use. Indeed, see for example FIGS. 11 and 17, they comprise mechanical connection means 36 and hydraulic connection means 38. A membrane 40 ensures the sterility of the hydraulic connection means 38, which are those involved in the passage of the therapeutic substance. The membrane 40 must be broken or removed in order to be able to couple the desired vial 34 with the respective access point 32. During the therapeutic treatment the vial 34 is left fitted onto the access point 32 even when it no longer contains any drugs, thus protecting the access point from any external contamination. At the end of the treatment the insert 30 is disposed of together with the vial 34 fitted onto it and the entire disposable tubing set 126.

In accordance with some embodiments, the vial 34 also comprises mechanical connection means 42 and hydraulic connection means 44. A membrane 46 ensures the sterility of the hydraulic connection means 44, which are those involved in the passage of the therapeutic substance. The membrane 46 must be broken or removed in order to be able to couple the vial 34 with the respective access point 32.

Figure 14:
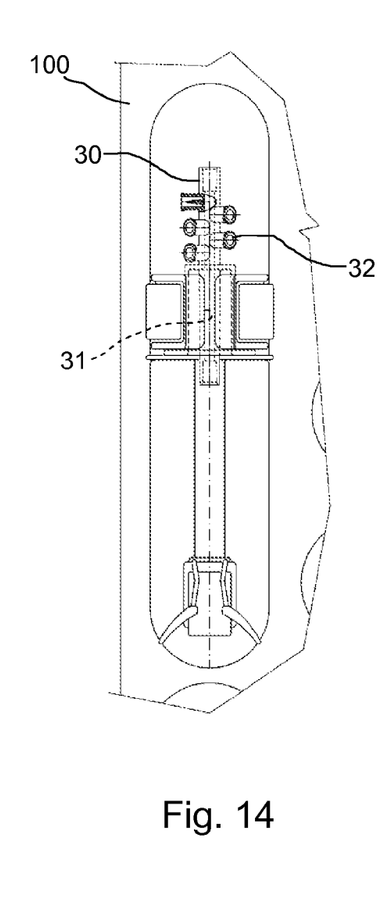
FIG. 14 represents a front view of another insert of a tubing set according to the invention applied to a known machine.
Figure 15:
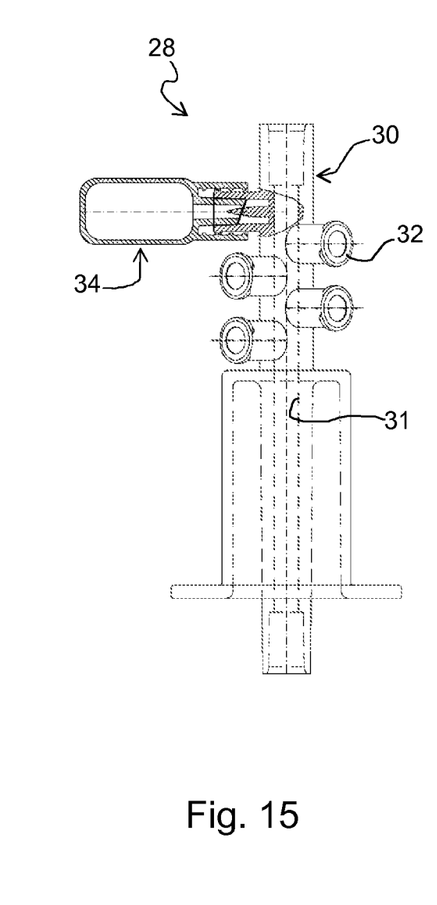
FIG. 15 represents a front view, partially in section, of the assembly comprising the insert of FIG. 14 and a vial fitted onto it.

FIGS. 9 to 13 show a first embodiment of the insert 30 having an overall parallelepiped shape and in which the access points 32 are arranged on the same face of the parallelepiped and have axes parallel to one another. FIGS. 14 and 15 show a second embodiment of the insert 30 having an overall tube shape and in which the access points 32 are arranged radially around the tube.

Figure 9:
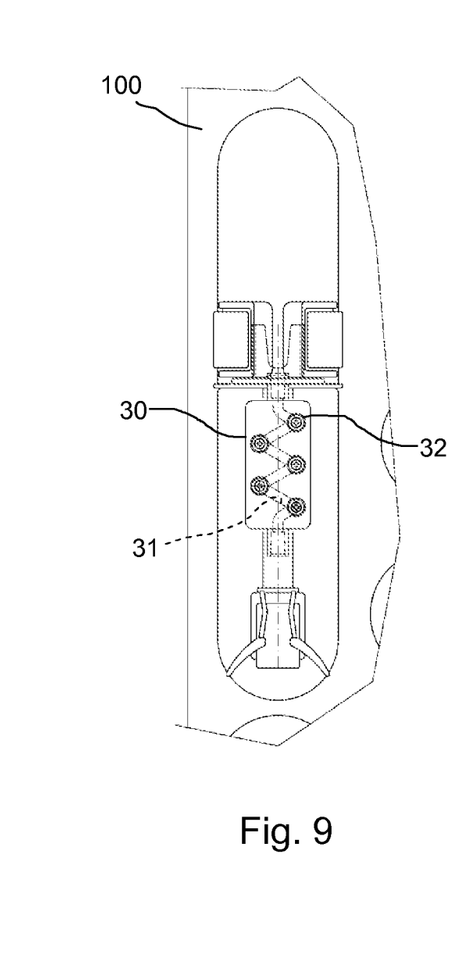
FIG. 9 represents a front view of an insert of a tubing set according to the invention applied to a known machine.
Figure 10:
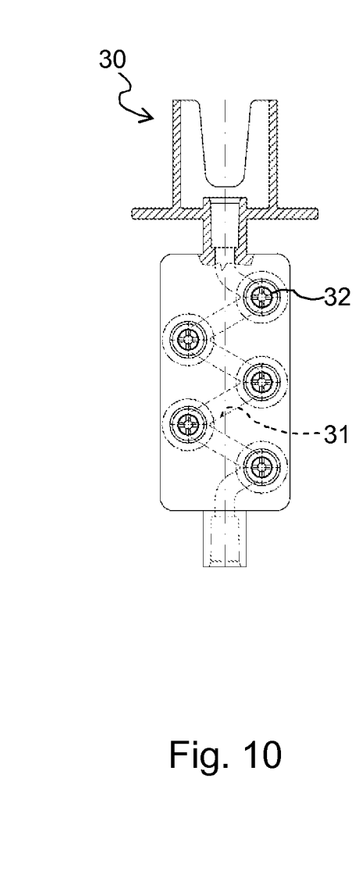
FIG. 10 represents a front view partially in section of the insert of FIG. 9.

In a known way, the machine 100 comprises a housing of a suitable shape and size for the insertion of the standard heparin syringe. In accordance with an embodiment, the insert 30 has the shape and size of a standard heparin syringe, so as to be able to be positioned in such a housing instead of the heparin syringe. Such a solution is represented in FIGS. 9 and 14.

Figure 1:
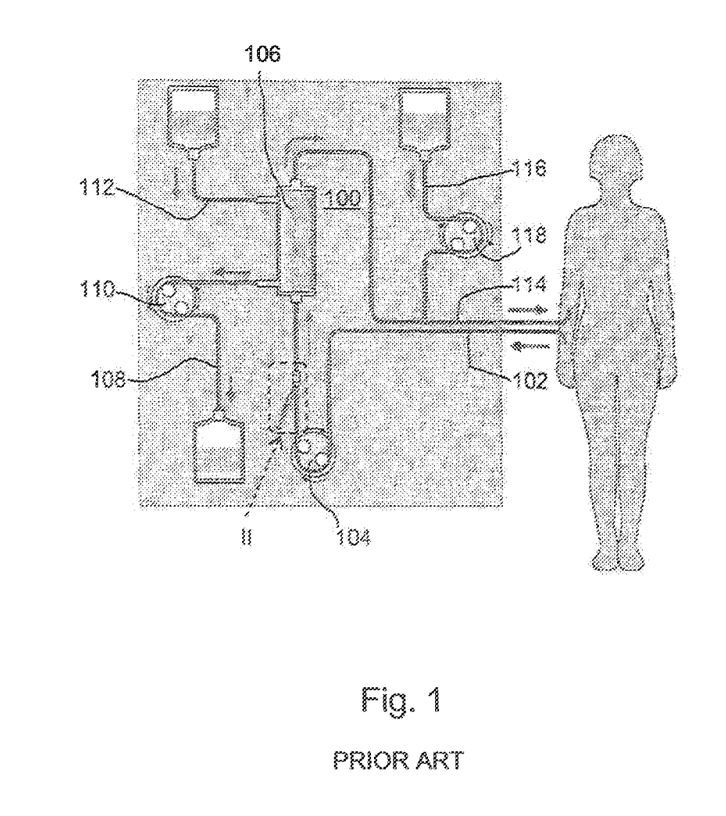
FIG. 1 schematically represents an extracorporeal circuit used in a hemodialysis treatment according to the prior art.
Figure 2:
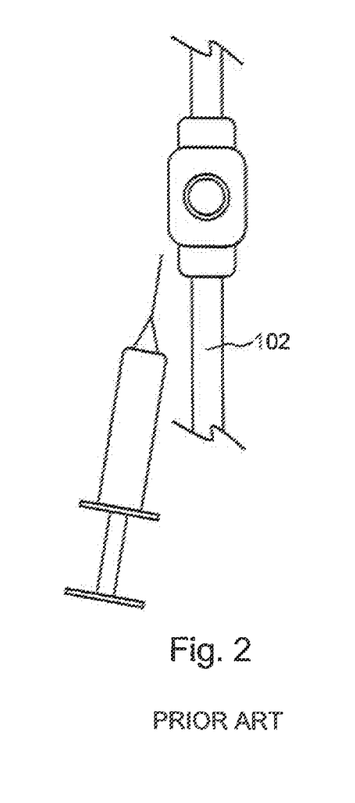
FIG. 2 schematically represents the detail, indicated with II in FIG. 1, of the puncturable cap for administering substances according to the prior art.
Figure 3:
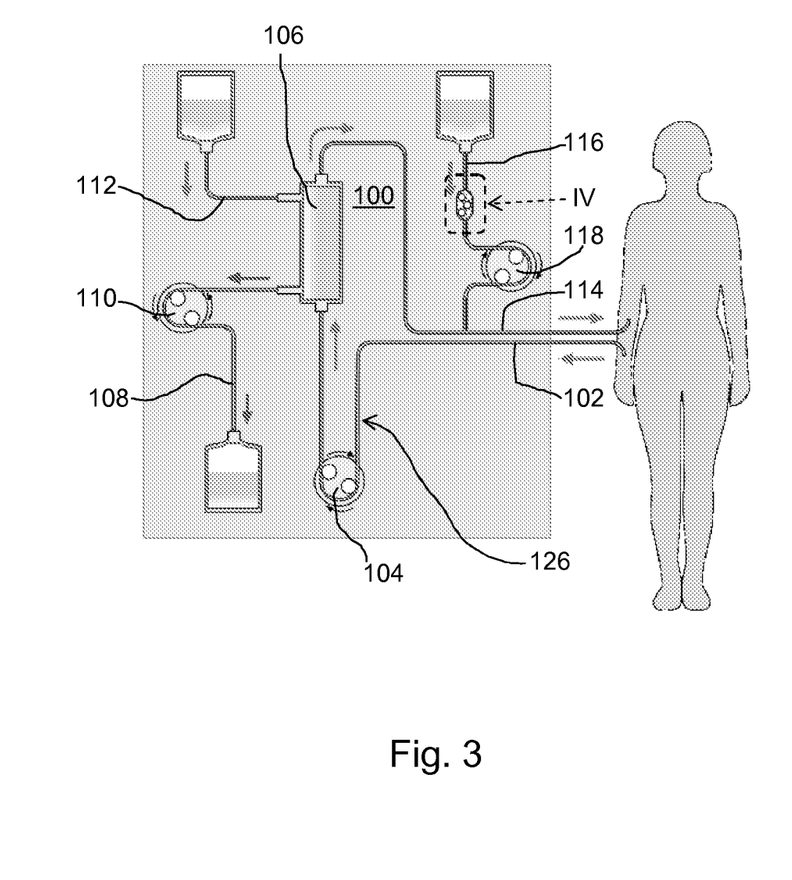
FIG. 3 schematically represents an extracorporeal circuit used in a hemodialysis treatment according to the invention.
Figure 4:
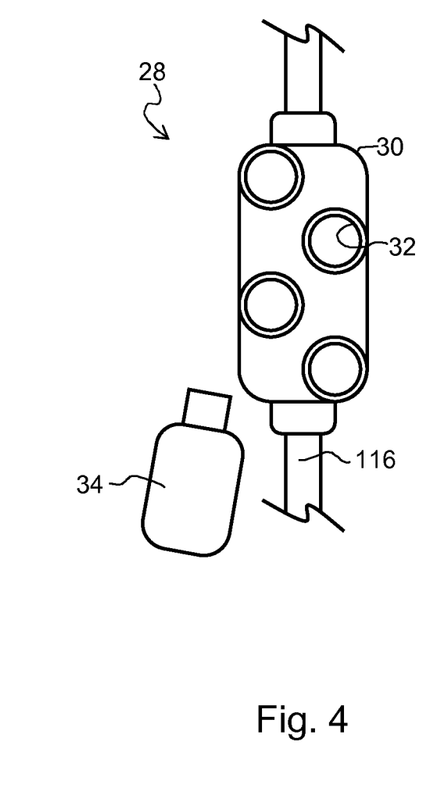
FIG. 4 schematically represents the detail, indicated with IV in FIG. 3, of the assembly for administering substances according to the invention.
Figure 5:
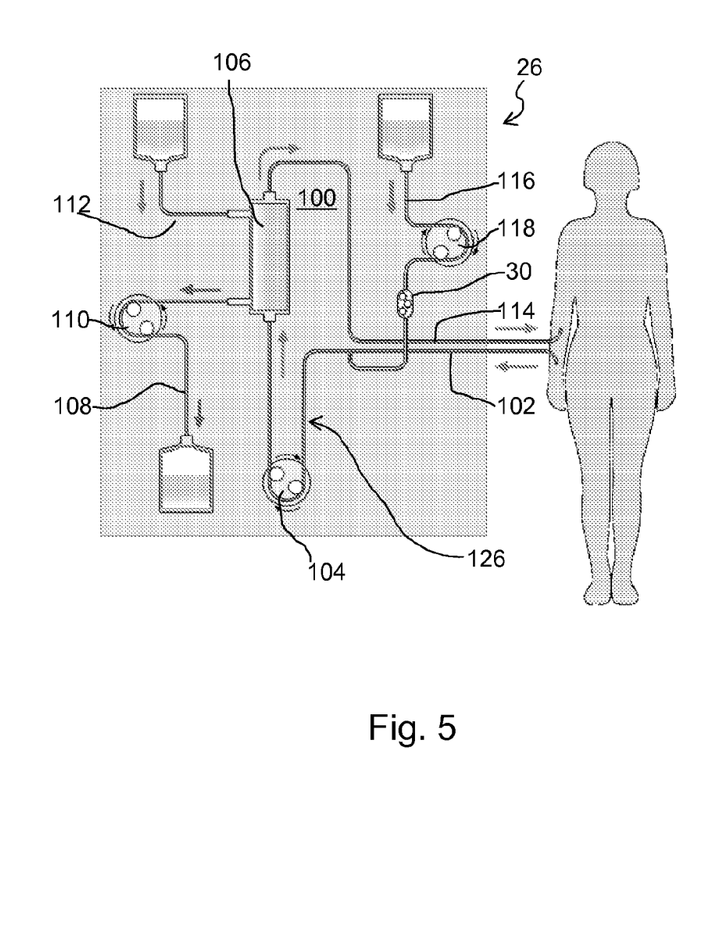
FIG. 5 schematically represents another extracorporeal circuit used in a hemodialysis treatment according to the invention.
Figure 6:
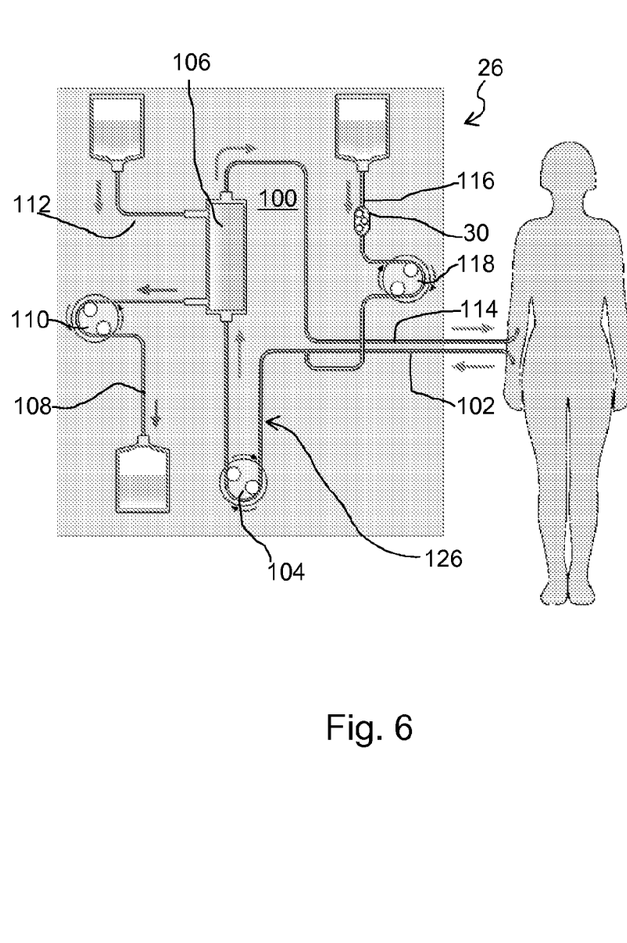
FIG. 6 schematically represents a further extracorporeal circuit used in a hemodialysis treatment according to the invention.
Figure 7:
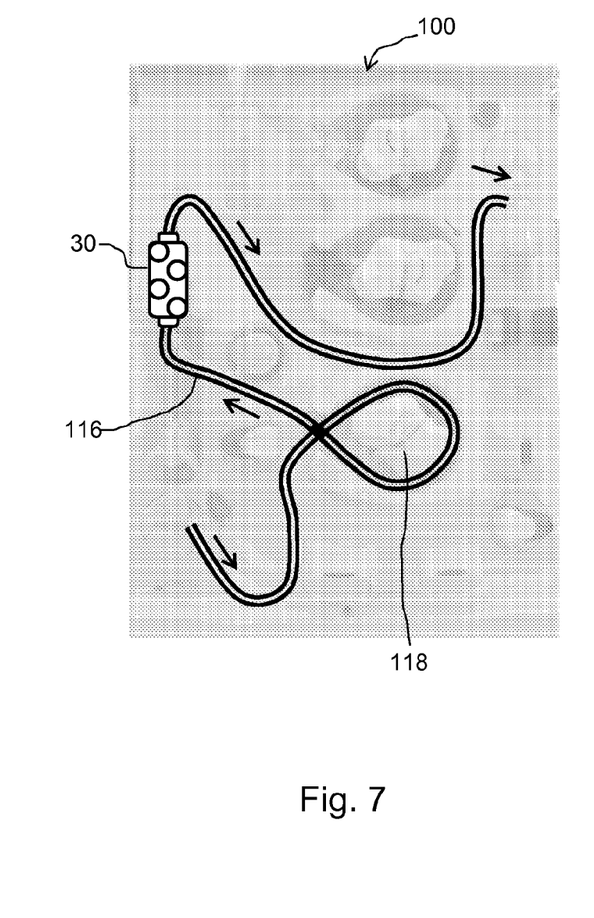
FIG. 7 schematically represents an extracorporeal circuit comprising an insert according to the invention in a first configuration.
Figure 8:
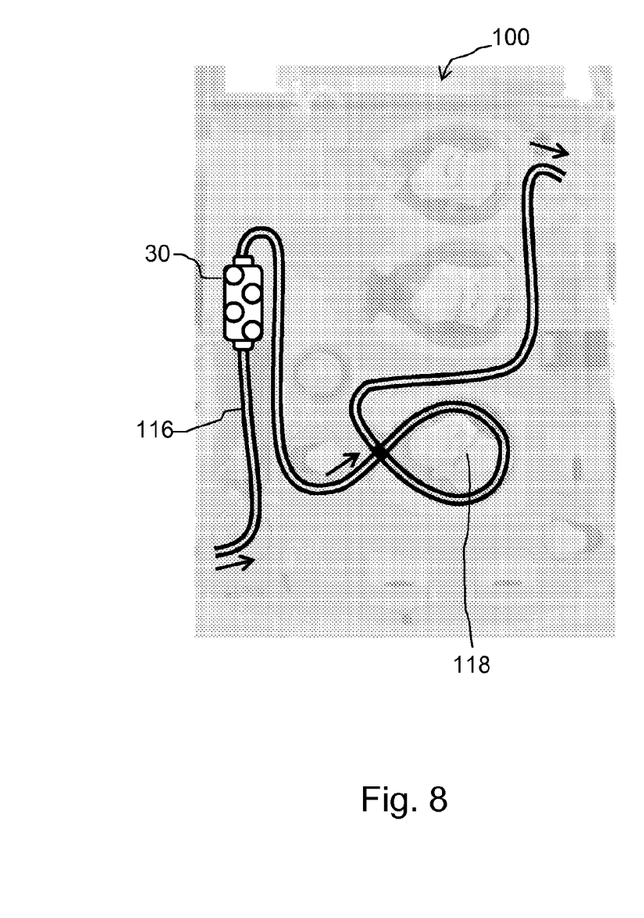
FIG. 8 schematically represents an extracorporeal circuit comprising an insert according to the invention in a second configuration.

In accordance with some configurations of the tubing set 126 according to the invention, for example that of FIG. 7, the insert 30 can be arranged downstream of the substitution pump 118. In these configurations, therefore, the substitution fluid which reaches the insert 30 is at a higher pressure than atmospheric pressure. In accordance with some other configurations of the tubing set 126 according to the invention, for example that of FIG. 8, the insert 30 can, on the other hand, be arranged upstream of the substitution pump 118. In these configurations, therefore, the substitution fluid which reaches the insert 30 is at a lower pressure than atmospheric pressure.

From what has been stated above, the person skilled in the art will understand that the dispensing of the substance contained inside the vial 34 will be carried out in different ways according to the case. Such ways shall be outlined later, with reference also to the different possible configurations for the vials 34 themselves.

The substitution tube 116 is advantageously used for the infusion of the therapeutic substances instead of the blood out-tube 102 or blood in-tube 114. The insert 30 according to the invention is therefore arranged along substitution tube 116 rather than along the blood tubes 102, 114.

The vials 34 according to the invention can be made from glass or, advantageously, polymeric material. Concerning this, it should be noted that not all therapeutic substances can be contained in polymeric vials. For some of them it is necessary to provide glass vials.

The polymeric vials can, for example, be made from polypropylene through blow-moulding. Of course, other polymers and other technologies can, if needed, satisfy specific particular requirements. The polymeric vials can advantageously be squeezed, so as to expel the substance contained in it. Should the vial 34 be fitted onto an insert 30 arranged upstream of the substitution pump 118, the depression inside the substitution tube 116 autonomously sucks up the substance contained in the vial 34. The possibility of the substance being dispensed in this way is ensured by the fact that the polymeric vial 34 can collapse as the volume of substance contained inside it reduces.

If, on the other hand, the insert 30 is arranged downstream of the substitution pump 118, the substitution tube 116 is under pressure. In this case, to dispense the substance contained in the vial 34, it is necessary to apply a pressure at least slightly greater than that present in the substitution tube 116. In this case, and should the substance be able to be dispensed in a single solution instead of a little at a time, it is for example possible to manually squeeze the vial 34.

The vials 34 made from glass, of course, do not allow these ways of dispensing the contained substances. In this case, the access point 32 of the insert 30 according to the invention can be configured so as to induce an internal washing of the vial 34 in order to remove its content.

One particular embodiment of the access point 32 that allows such washing is described hereafter with reference to FIGS. 16 to 22.

Figure 16:
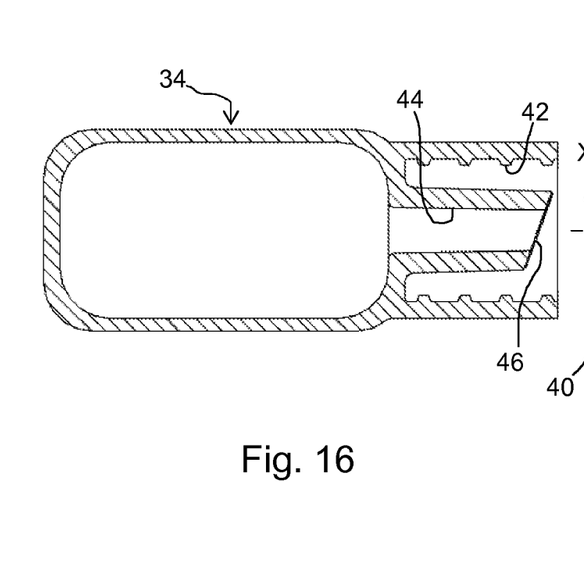
FIG. 16 represents a detailed section view of a vial according to the invention suitable for being fitted onto an insert according to the invention.
Figure 17:
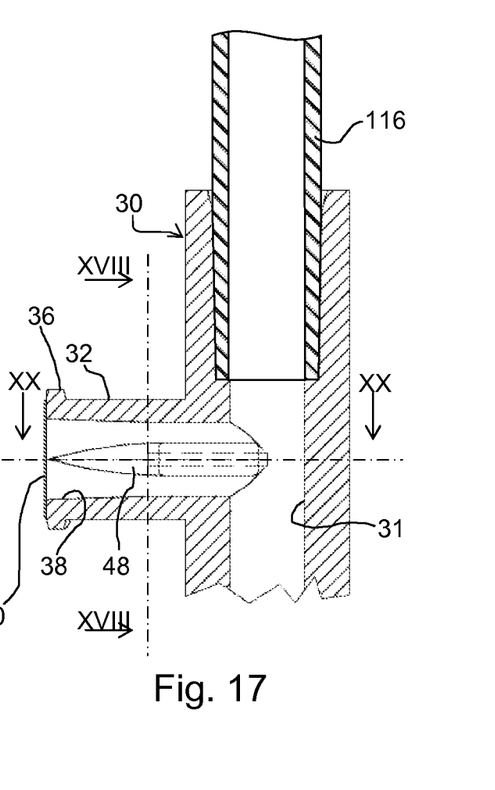
FIG. 17 represents a detailed section view of an insert according to the invention suitable for receiving the fitting of the vial of FIG. 16.
Figure 18:
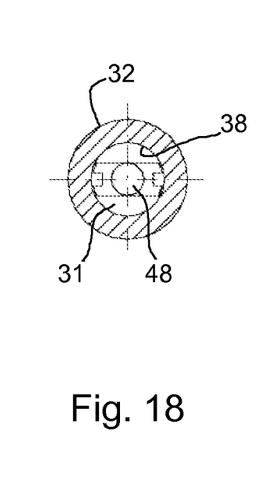
FIG. 18 represents a section view along the line XVIII-XVIII of FIG. 17.
Figures 19, 20:
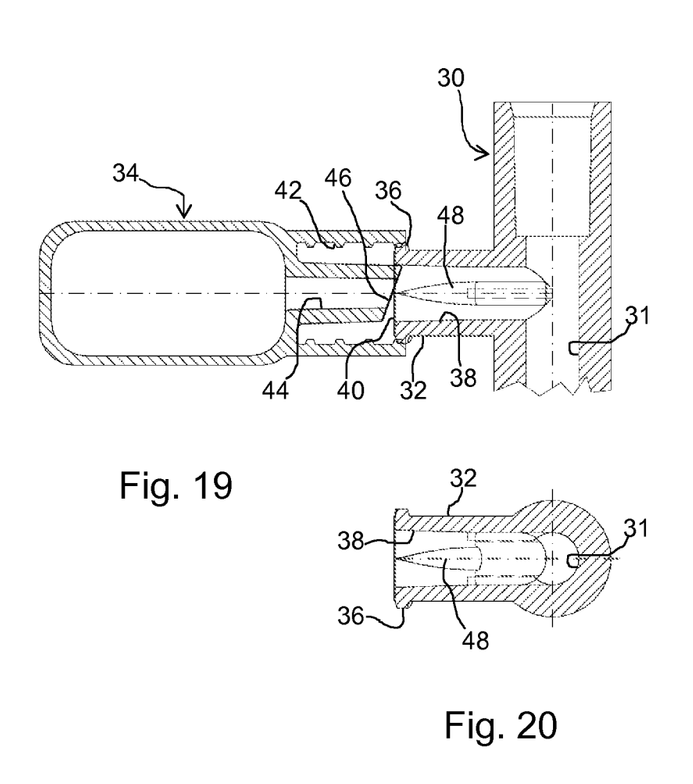
FIG. 19 represents a section view of the vial of FIG. 16 brought up to the insert of FIG. 17.
FIG. 20 represents a section view along the line XX-XX of FIG. 17.
Figures 21, 22:
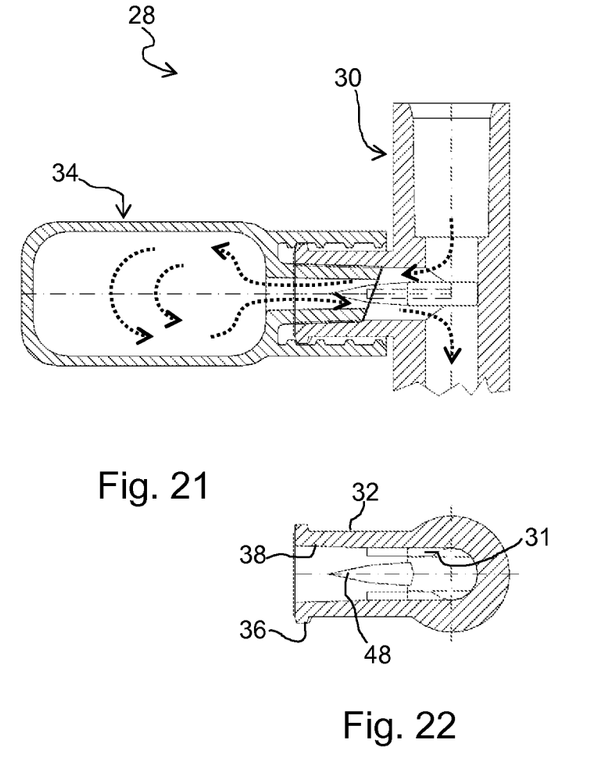
FIG. 21 represents a section view of the assembly according to the invention comprising the insert of FIG. 17 and the vial of FIG. 16 fitted onto it.
FIG. 22 represents a section view similar to that of FIG. 20 in a different configuration.

FIG. 16 illustrates a vial 34 according to the invention made from glass. FIG. 17 illustrates, in section, an access point 32 according to the invention. Such an access point 32 comprises a movable spike 48. As can be seen in FIG. 19, the action of bringing the vial 34 up to the access point 32 involves firstly breaking the membrane 40 that protects the hydraulic connection means 38. Continuing in the action of fitting the vial 34, the movable spike 48 makes contact with the membrane 46 of the vial itself, in turn breaking it. Continuing further in the fitting, the movable spike 48 makes contact with the hydraulic connection means 44 of the vial 34 and is pushed by them towards the inside of the insert 30. The final effect of this movement of the movable spike 48 can be seen by comparing FIGS. 19 and 21 and, respectively, 20 and 22. In the final configuration shown in FIGS. 21 and 22, the root of the movable spike 48 at least partially obstructs the main duct 31 of the insert 30. The flow prevented in the main duct 31 is thus deviated inside the vial 34. The main flow enters into the vial 34, mixes with the substance originally contained in it and finally comes out, pushed by the new fluid deviated by the root of the movable spike 48. The aforementioned washing is thus obtained, schematically indicated by the dotted arrows in FIG. 21.

The washing described above is obtained for a vial 34 according to the invention, comprising single hydraulic connection means 44. A different washing system can be obtained with a different vial 34, of the type illustrated in FIGS. 23 to 26. Such a vial comprises double connection means: first mechanical connection means 42' and first hydraulic connection means 44' suitable for being fitted onto an access point 32; and second mechanical connection means 42" and second hydraulic connection means 44" arranged substantially at the opposite ends of the vial 34. In this case a flow of substitution fluid enters through the second hydraulic connection means 44" into the vial 34, mixes with the substance contained in it and finally comes out, through the first hydraulic connection means 44'.

Figure 23:
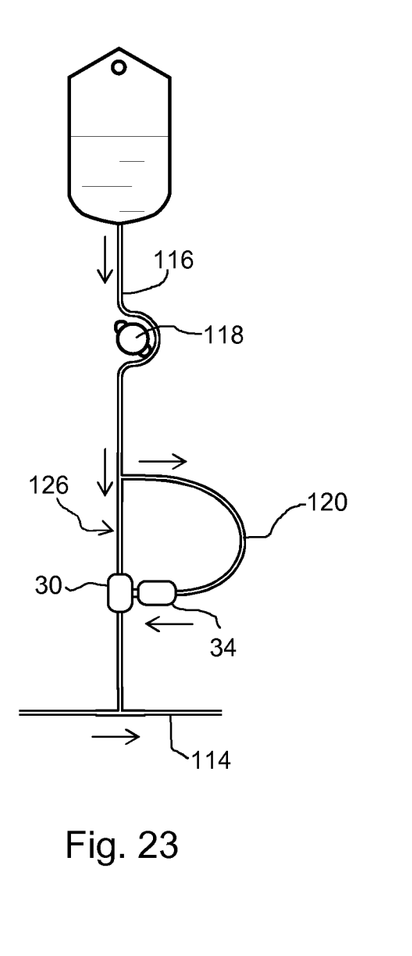
FIG. 23 schematically represents a portion of a tubing set according to the invention in an extracorporeal circuit.

In accordance with the embodiment schematically shown in FIG. 23, the insert 30 is placed along the substitution tube 116. In such embodiment, the substitution tube 116 comprises a secondary branch 120 diverting from the substitution tube 116 and connecting again with it. The insert 30 is placed at the connection between the secondary branch 120 and the substitution tube 116. The substitution fluid which enters into the vial 34 comes from the secondary branch 120 and flows again into the substitution tube 116.

Figure 24:
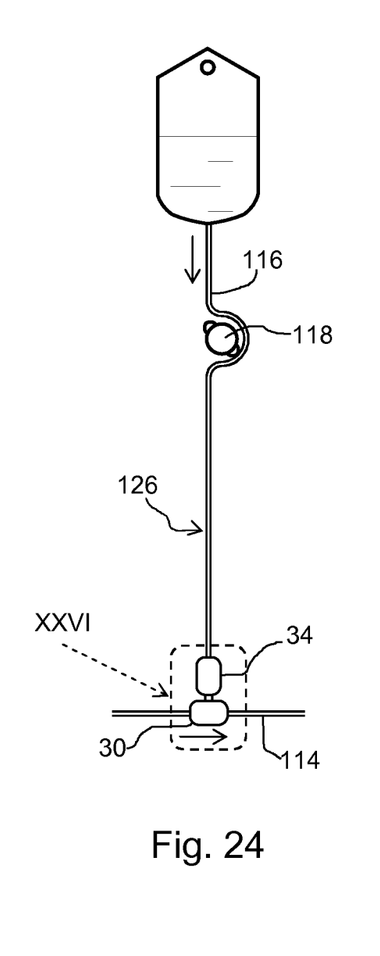
FIG. 24 schematically represents a portion of another tubing set according to the invention in an extracorporeal circuit.
Figure 25:
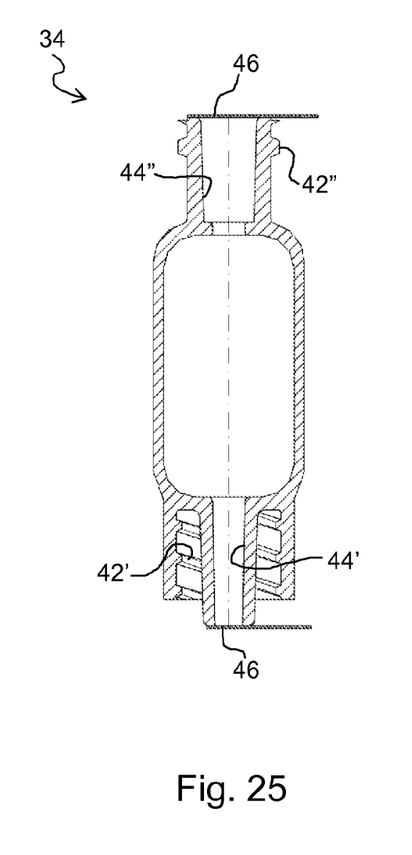
FIG. 25 represents a detailed section view of another vial according to the invention suitable for being fitted onto an insert in a tubing set according to the invention.
Figure 26:
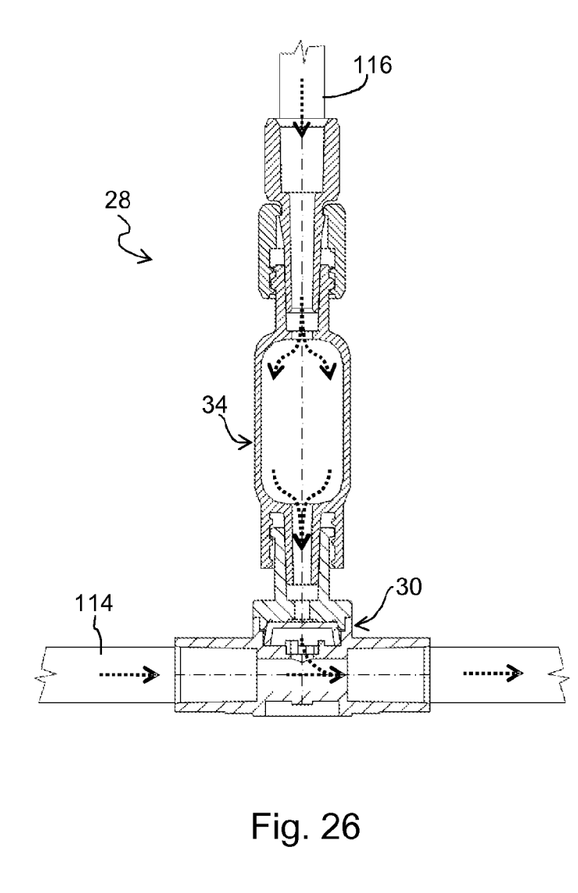
FIG. 26 represents the detail, indicated with XXVI in FIG. 24, i.e. represents the vial of FIG. 25 coupled with an insert in the tubing set according to the invention.

In accordance with the embodiment schematically shown in FIG. 24, the insert 30 is placed at the connection of the substitution tube 116 with the blood in-tube 114. In such embodiment, the flow that enters into the vial 34 is the whole substitution fluid flow immediately upstream of the convergence with the blood in-tube 114. According to a different embodiment of the tubing set 126, the insert 30 can be placed at the connection of the substitution tube 116 with the blood out-tube 102.

The same concepts for dispensing the content of the vial 34 through washing can be exploited for polymeric vials when fitted downstream of the substitution pump 118.

In view of the above description, the skilled person can appreciate that the tubing set 126 according to the invention allows to perform automated processes for the delivery of any medicament. In fact, the particular arrangement of the tubing set 126 according to the invention permits to utilize the flow of the substitution fluid for automatically sucking the drug out of any vial, either collapsible or rigid. Such solution allows administering of drugs without needing the active presence of the service staff, even if a slow release is needed.

In accordance with some embodiments, see for example FIGS. 3 to 15, the insert 30 comprises a plurality of access points 32. The plurality of access points 32 allows multiple and simultaneous dispensing of drugs and/or therapeutic substances.

The invention relates finally to a method for delivering drugs into the extracorporeal blood circuit of a hemodialysis machine. The method according to the invention comprises the steps of:
  connecting a blood out-tube 102 to the patient for supplying the blood to a filter 106 of the hemodialysis machine 100;
  connecting a blood in-tube 114 to the patient for supplying the blood from the filter 106 back to the patient; and
  connecting a substitution tube 116 to one of said blood in-tube 114 or blood out-tube 102 for providing a substitution fluid to replace the waste water removed from the blood by the filter 106 during the hemodialysis treatment, said substitution tube 116 comprising an insert 30 for the infusion of drugs; and
  infusing a drug by means of said insert 30 into said substitution fluid.

According to an embodiment of the method, the step of infusing a drug into said substitution fluid comprises the step of connecting a vial 34 to the insert 30 and, preferably, using the flow of the substitution fluid for automatically sucking the drug out of the vial.

In view of the above description, the skilled person will easily appreciate that the present invention overcomes most of the drawbacks pointed out with respect to the prior art. In fact, the present invention allows to automatically deliver any medicament in an extracorporeal circuit in a lot of different conditions. Specifically, the delivery can be carried out up- or downstream the filter, up- or downstream the substitution pump, from collapsible or rigid vials, and with different delivery rates.

The person skilled in the art can bring modifications and/or replacements of described element with equivalent elements to the embodiments of the tubing set 126, of the insert 30 and of the vial 34 according to the invention described above, in order to satisfy specific requirements, without for this reason departing from the scope of the attached claims.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A tubing set suitable for use in co-operation with a machine for carrying out a hemodialysis treatment of a patient's blood, said tubing set comprising:
  a blood out-tube for supplying the blood from the patient to a filter of said machine;
  a blood in-tube for supplying the blood from the filter back to the patient; and
  a substitution tube connected to one of said blood in-tube or said blood out-tube, said substitution tube being configured to provide a substitution fluid to the patient's blood and including an insert configured for connection to a vial for infusing a drug to the substitution fluid,
  said insert including a main duct that provides fluid continuity in the substitution tube,
  an access point at which the vial is connectable to the insert, said access point including a mechanical connector that is connectable to a corresponding mechanical connector of the vial, and a fluid conduit that communicates with a corresponding fluid conduit of the vial,
  a membrane that provides for sterility of the fluid conduits, and
  a movable spike,
  the membrane being breakable by the movable spike so as to place the insert in fluid communication with the vial,
  said insert being configured such that a portion of the substitution fluid being communicated in the main duct of the insert is diverted therefrom by the movable spike so as to enter the vial and to convey the drug therein from the vial and to the substitution tube.

2. The tubing set according to claim 1, further comprising a drain tube for discharging a waste fluid originating from the filter; and
  a dialysate tube for supplying a dialysate to the filter.

3. The tubing set according to claim 2, wherein said blood out-tube, said drain tube, and said substitution tube are configured to co-operate, respectively, with a blood pump, a drain pump, and a substitution pump of said machine.

4. The tubing set according to claim 1, wherein said insert is placed at a connection between said substitution tube and said blood in-tube or said blood out-tube.

5. The tubing set according to claim 1, wherein said substitution tube includes a secondary branch that diverts from the substitution tube and that reconnects with the substitution tube.

6. The tubing set according to claim 5, wherein said insert is placed at a connection between said secondary branch and said substitution tube.

7. The tubing set according to claim 1, wherein said insert has a shape and a size consistent with that of a heparin syringe associated with such a machine, such that the insert is positionable in a housing of the machine configured for the insertion of the heparin syringe.

* * * * *

UNITED STATES PATENT AND TRADEMARK OFFICE
CERTIFICATE OF CORRECTION

PATENT NO. : 9,623,227 B2
APPLICATION NO. : 13/498681
DATED : April 18, 2017
INVENTOR(S) : Reinhold Reiter et al.

It is certified that error appears in the above-identified patent and that said Letters Patent is hereby corrected as shown below:

Item (73) Assignee:

Please change "Presenius Medical Care Deutschland GmbH" to -- Fresenius Medical Care Deutschland GmbH--

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*